(12) United States Patent
Okamoto et al.

(10) Patent No.: US 12,734,342 B2
(45) Date of Patent: Sep. 15, 2026

(54) BALLOON FOR CATHETER

(71) Applicant: GOODMAN CO., LTD., Nagoya (JP)

(72) Inventors: Mitsumasa Okamoto, Seto (JP); Takuma Miyamura, Seto (JP); Shizuya Yoshinaga, Seto (JP); Shoma Kondo, Seto (JP); Shuhei Yamamoto, Seto (JP); Yuta Nakamura, Seto (JP)

(73) Assignee: GOODMAN CO., LTD., Nagoya (JP)

( * ) Notice: Subject to any disclaimer, the term of this patent is extended or adjusted under 35 U.S.C. 154(b) by 40 days.

(21) Appl. No.: 18/441,668

(22) Filed: Feb. 14, 2024

(65) Prior Publication Data

US 2024/0181225 A1 Jun. 6, 2024

Related U.S. Application Data

(63) Continuation of application No. PCT/JP2022/028565, filed on Jul. 25, 2022.

(30) Foreign Application Priority Data

Aug. 16, 2021 (JP) ................................ 2021-132154

(51) Int. Cl.
*A61M 25/10* (2013.01)

(52) U.S. Cl.
CPC ..... *A61M 25/10* (2013.01); *A61M 2025/1075* (2013.01); *A61M 2025/1084* (2013.01)

(58) Field of Classification Search
CPC .......... A61M 25/10; A61M 2025/1075; A61M 2025/1084; A61M 25/1002;
(Continued)

(56) References Cited

U.S. PATENT DOCUMENTS 5,470,314 A * 11/1995 Walinsky ............ A61M 25/104 604/528
6,544,224 B1 * 4/2003 Steese-Bradley ............................ A61M 25/1029 604/103.08
(Continued)

FOREIGN PATENT DOCUMENTS

CN 112203712 A 1/2021
EP 2292185 A1 3/2011
(Continued)

OTHER PUBLICATIONS

May 14, 2024—(JP) Notification of Reason for Rejection—JP App 2023-542286, Eng Tran, 8 pages.
(Continued)

*Primary Examiner* — Andrew Restaino
(74) *Attorney, Agent, or Firm* — Banner & Witcoff, Ltd.

(57) ABSTRACT

A balloon for a catheter includes an inflatable portion, a distal end connecting portion, and a proximal end connecting portion. The balloon for the catheter also includes an inner side thick film portion and a thin film portion having differing thicknesses from each other. The thickness of the inner side thick film portion is greater than the thickness of the thin film portion. An inner surface at the inner side thick film portion protrudes further toward an inner side than an inner surface at the thin film portion. An outer surface at the inner side thick film portion does not protrude further to an outer side in the radial direction than an outer surface at the thin film portion.

7 Claims, 7 Drawing Sheets

(58) Field of Classification Search
CPC ........ A61M 25/104; A61M 2025/1031; A61M 2025/107; A61M 25/1029; A61M 2025/1086; A61F 2/958; A61F 2002/9586
See application file for complete search history.

(56) References Cited

U.S. PATENT DOCUMENTS

| | | | | |
|---|---|---|---|---|
| 11,679,242 | B2 | 6/2023 | Okamoto et al. | |
| 2002/0010489 | A1 | 1/2002 | Grayzel et al. | |
| 2003/0028211 | A1 | 2/2003 | Crocker et al. | |
| 2005/0102020 | A1 | 5/2005 | Grayzel et al. | |
| 2006/0015133 | A1 | 1/2006 | Grayzel et al. | |
| 2006/0129179 | A1* | 6/2006 | Weber | A61M 25/1029 604/264 |
| 2006/0182873 | A1 | 8/2006 | Klisch et al. | |
| 2007/0244501 | A1 | 10/2007 | Horn et al. | |
| 2008/0177228 | A1* | 7/2008 | Burton | B29C 49/04112 425/523 |
| 2010/0234874 | A1 | 9/2010 | Burton | |
| 2011/0077677 | A1 | 3/2011 | Grayzel et al. | |
| 2011/0213401 | A1 | 9/2011 | Grayzel et al. | |
| 2018/0085562 | A1 | 3/2018 | Grayzel et al. | |
| 2018/0280666 | A1* | 10/2018 | Yamazaki | A61B 17/12136 |
| 2019/0240464 | A1 | 8/2019 | Giasolli et al. | |
| 2020/0276417 | A1* | 9/2020 | Rentschler | A61M 25/1029 |
| 2021/0113821 | A1 | 4/2021 | Okamoto et al. | |

FOREIGN PATENT DOCUMENTS

| | | | |
|---|---|---|---|
| JP | 2004-504111 | A | 2/2004 |
| JP | 2008-529740 | A | 8/2008 |
| JP | 2009-534094 | A | 9/2009 |
| JP | 6259560 | B2 | 1/2018 |

OTHER PUBLICATIONS

Oct. 18, 2022—International Search Report—Intl App PCT/JP2022/028565, 5 pages.

Feb. 13, 2024—(WO) International Preliminary Report on Patentability—Intl App PCT/JP2022/028565, Eng Tran, 5 pages.

Nov. 20, 2025—(CN) First Office Action—App 202280021608.5.

Jul. 3, 2025—(EP) Extended EP Search Report—EP App 22858257.3.

* cited by examiner

BALLOON FOR CATHETER

REFERENCE TO RELATED APPLICATIONS

This application is a Continuation Application of International Application No. PCT/JP2022/028565, filed Jul. 25, 2022, which claims priority from Japanese Patent Application No. 2021-132154, filed on Aug. 16, 2021. This disclosure of the foregoing application is hereby incorporated by reference in its entirety.

BACKGROUND ART

In a balloon catheter, the balloon is required to withstand high pressure, and various methods are proposed to secure the high-pressure resistance of the balloon. For example, a balloon catheter that includes a base balloon is known. By providing a reinforcing portion on the outer surface of the base balloon, the base balloon is caused to be high-strength and excessive inflation is suppressed when the base balloon is pressurized.

SUMMARY

When a balloon has a structure that is thick at an external portion, there is a problem that the passability of the balloon inside the blood vessel deteriorates. Further, when the balloon is used to retain a stent inside the blood vessel, the balloon is more easily caught up on the stent due to the thickness provided at the external portion of the balloon. In this case, the problem is that there is a possibility of a deterioration in the passability of the balloon past the stent that is retained inside the blood vessel, or of it becoming more difficult to remove the balloon from the stent after the dilation of the stent by the balloon.

An object of the present disclosure is to provide a balloon for a catheter capable of maintaining passability inside a blood vessel while realizing high-pressure resistance.

A balloon for a catheter of the present disclosure includes an inflatable portion, a distal end connecting portion, and a proximal end connecting portion. The inflatable portion has a tube shape and extends in an extending direction. The distal end connecting portion is a portion extending from a first distal end portion, that is an end portion on one side in the extending direction of the inflatable portion, to the opposite side to the inflatable portion. A diameter of an end portion of the distal end connecting portion connected to the inflatable portion is larger than a diameter of a second distal end portion that is an end portion on the opposite side from the end portion connected to the inflatable portion. The proximal end connecting portion is a portion extending from a first proximal end portion, that is an end portion on another side in the extending direction of the inflatable portion. The diameter of an end portion of the proximal end connecting portion connected to the inflatable portion is larger than a diameter of a second proximal end portion that is an end portion on the opposite side from the end portion connected to the inflatable portion. The balloon for the catheter also includes an inner side thick film portion and a thin film portion having differing thicknesses from each other. The thickness of the inner side thick film portion is greater than the thickness of the thin film portion. An inner surface at the inner side thick film portion protrudes further toward an inner side than an inner surface at the thin film portion, in a radial direction centered on a center axis extending in the extending direction and passing through a center of the inflatable portion. An outer surface at the inner side thick film portion does not protrude further to an outer side in the radial direction than an outer surface at the thin film portion.

The balloon for a catheter can suppress rapid inflation using the inner side thick film portion, and high-pressure resistance is thus possible. The outer surface at the inner side thick film portion does not protrude further to the outer side in the radial direction than the outer surface at the thin film portion. Thus, the balloon for a catheter can maintain excellent passability inside a blood vessel.

BRIEF DESCRIPTION OF DRAWINGS

Embodiments will be described below in detail with reference to the accompanying drawings in which.

DESCRIPTION OF EMBODIMENTS

Embodiments (1A to 1G) of a balloon catheter 1 according to the present disclosure will be explained with reference to the drawings. The referenced drawings are used to describe technical features that can be employed in the present disclosure. The described configurations and the like of the device are not intended to be limited thereto, and are merely examples for explanation purposes. Using a balloon 3, the balloon catheter 1 can dilate a stenotic lesion formed in a blood vessel, or can dilate a stent inside the blood vessel.

First Embodiment (Balloon Catheter 1A)

Figure 1:
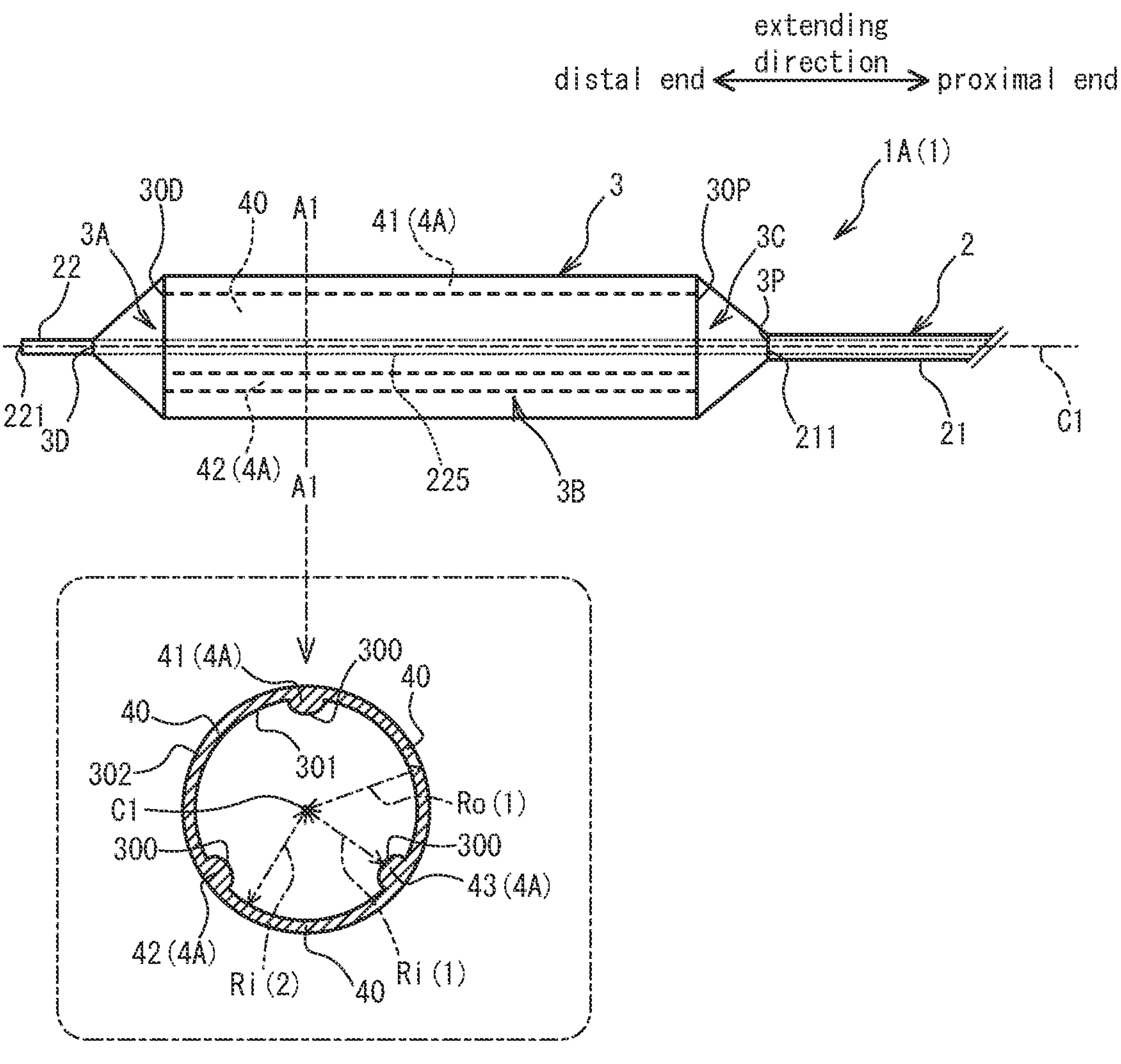
FIG. 1 is a view showing a balloon catheter, and a cross-sectional view when the balloon catheter is cut on a plane orthogonal to an extending direction.

The balloon catheter 1A will be described with reference to FIG. 1. The balloon catheter 1A includes a catheter shaft 2 and the balloon 3.

Catheter Shaft 2

The balloon 3 is connected to an end portion on one side of the tube-shaped catheter shaft 2. The balloon catheter 1A is used in a state in which a hub, not shown in the drawings, is connected to an end portion on the other side of the catheter shaft 2. The hub can supply compressed fluid to the balloon 3 via the catheter shaft 2.

Hereinafter, the one side from among both ends of the catheter shaft 2 will be referred to as a distal end side. The other side from among both ends of the catheter shaft 2 will be referred to as a proximal end side. The direction extending along the catheter shaft 2 will be referred to as to as an extending direction. An axis passing through the center of the catheter shaft 2 and extending in the extending direction will be referred to as a center axis C1. In a cross section cut on a plane orthogonal to the center axis C1 (hereinafter simply referred to as a cross section), the side closer to the center axis C1 in a radial direction centered on the center axis C1 will be referred to as an inner side, and the side further away from the center axis C1 will be referred to as to as an outer side.

The catheter shaft 2 has an outer tube 21 and an inner tube 22. The outer tube 21 and the inner tube 22 are both flexible. The inside diameter of the outer tube 21 is larger than the outside diameter of the inner tube 22. Apart from a predetermined portion on the distal end side, the inner tube 22 is disposed inside the lumen of the outer tube 21. The predetermined portion on the distal end side of the inner tube 22 protrudes toward the distal end side from an end (hereinafter referred to as a distal end 211) on the distal end side of the outer tube 21. The end (hereinafter referred to as a distal end 221) on the distal end side of the inner tube 22 is disposed further to the distal end side than the distal end 211 of the outer tube 21. Hereinafter, the predetermined portion on the distal end side of the inner tube 22 will be referred to as a protruding section 225. The material of the outer tube 21 and the inner tube 22 is not particularly limited, and a polyamide resin may be used, for example.

The compressed fluid supplied from the hub passes through a space of the lumen of the outer tube 21 other than the lumen of the inner tube 22. A guide wire that is not shown in the drawings is inserted through the lumen of the inner tube 22.

Balloon 3

The balloon 3 can change shape between a deflated state and an inflated state, as a result of a change in internal pressure according to whether the compressed fluid is supplied from the hub that is not shown in the drawings. FIG. 1 shows the balloon 3 in the inflated state. The end (hereinafter referred to as a distal end portion 3D) on the distal end side of the balloon 3 is connected by thermal welding to the inner tube 22, in the vicinity of the distal end 221 of the protruding section 225. Further, the end (hereinafter referred to as a proximal end portion 3P) on the proximal end side of the balloon 3 is connected by thermal welding to the outer tube 21, in the vicinity of the distal end 211. The balloon 3 covers the protruding section 225 of the inner tube 22 from the outside. The material of the balloon 3 is not particularly limited, and a polyamide resin may be used, for example.

A distal end connecting portion 3A, an inflatable portion 3B, and a proximal end connecting portion 3C are defined in the balloon 3. The distal end connecting portion 3A is a region extending while increasing in diameter from the distal end portion 3D toward the proximal end portion 3P of the balloon 3 in the inflated state. The proximal end connecting portion 3C is a region extending while increasing in diameter from the proximal end portion 3P toward the distal end portion 3D of the balloon 3 in the inflated state. The inflatable portion 3B is a region sandwiched between the distal end connecting portion 3A and the proximal end connecting portion 3C of the balloon 3 and the diameter thereof is substantially the same along the extending direction in the inflated state. In the inflated state, the inflatable portion 3B has a tubular shape extending in the extending direction. The balloon 3 has an inner surface 301 and an outer surface 302. A distance in the radial direction from the center axis C1 to the inner surface 301 will be referred to as an inner radius Ri(n) (n is an integer). A distance in the radial direction from the center axis C1 to the outer surface 302 will be referred to as an outer radius Ro(n).

An end on the distal end side of the inflatable portion 3B will be referred to as a distal end portion 30D, and an end on the proximal end side of the inflatable portion 3B will be referred to as a proximal end portion 30P. The distal end connecting portion 3A extends to the distal end side toward the distal end portion 3D, from an end connected to the distal end portion 30D of the inflatable portion 3B. The diameter of a cross section of the distal end connecting portion 3A is largest at the end connected to the distal end portion 30D of the inflatable portion 3B, and is smallest at the distal end portion 3D. The proximal end connecting portion 3C extends to the proximal end side toward the proximal end portion 3P, from an end connected to the proximal end portion 30P of the inflatable portion 3B. The diameter of a cross section of the proximal end connecting portion 3C is largest at the end connected to the proximal end portion 30P of the inflatable portion 3B, and is smallest at the proximal end portion 3P.

The inflatable portion 3B of the balloon 3 includes inner side thick film portions 41, 42, and 43 (hereinafter referred to as an inner side thick film portion 4A when there is no particular distinction to be made), and thin film portions 40. The thickness differs between the inner side thick film portion 4A and the thin film portions 40. The thickness of the inner side thick film portion 4A is thicker than that of the thin film portions 40. The outer radius Ro(1) of the inflatable portion 3B is the same at the inner side thick film portion 4A and the thin film portions 40. Thus, the outer surface 302 of the inflatable portion 3B is smooth and has no indentations and protrusions. On the other hand, the inner radius Ri(n) of the inflatable portion 3B differs at the inner side thick film portion 4A and the thin film portions 40. The inner radius Ri(1) at the inner side thick film portion 4A is smaller than the inner radius Ri(2) at the thin film portions 40. Thus, the inner surface 301 of the inflatable portion 3B protrudes to the inner side at the inner side thick film portion 4A. Hereinafter, this portion will be referred to as a protruding portion 300. The protruding portion 300 curves in a convex shape toward the center axis C1.

The inner side thick film portion 4A extends from the distal end portion 30D to the proximal end portion 30P of the inflatable portion 3B along the extending direction. The inner side thick film portions 41, 42, and 43 are disposed at equal intervals in the circumferential direction centered on the center axis C1. The inner radius Ri(1) at the inner side thick film portion 4A is uniform from the distal end portion 30D to the proximal end portion 30P. In other words, a protrusion amount toward the center axis C1 of the protruding portion 300 formed in the inner surface 301 at the inner side thick film portion 4A is uniform from the distal end portion 30D to the proximal end portion 30P.

The thin film portions 40 are disposed between the inner side thick film portions 41 and 42, between the inner side thick film portions 42 and 43, and between the inner side thick film portions 43 and 41 in the circumferential direction.

Operations and Effects of First Embodiment

In the balloon catheter 1A, the thickness of the inflatable portion 3B of the balloon 3 is greater at the inner side thick film portion 4A than at the thin film portions 40. Thus, the balloon 3 can withstand the high pressure, since a rapid inflation can be suppressed by the inner side thick film portion 4A. The outer radius Ro(1) of the balloon 3 is the same at the inner side thick film portion 4A and the thin film portions 40, and there is no protrusion to the outer side even at the thicker inner side thick film portion 4A. Thus, the balloon catheter 1A can maintain excellent passability of the balloon 3 inside the blood vessel.

The inner side thick film portion 4A provided at the inflatable portion 3B can suppress the balloon 3 from rapidly expanding or contracting in the extending direction at a time of deflation or inflation. As a result, the balloon catheter 1A can suppress the distal end connecting portion 3A, the inflatable portion 3B, and the proximal end connecting portion 3C from rapidly widening in the radial direction in response to the expansion of the balloon 3 in the extending direction, and high pressure resistance is thus possible.

The inner side thick film portion 4A extends in the extending direction from the distal end portion 30D to the proximal end portion 30P of the inflatable portion 3B. Thus, the balloon catheter 1A can suppress the balloon 3 from rapidly expanding or contracting in the extending direction at the time of deflation and inflation across the whole region of the inflatable portion 3B. Further, by suppressing the increase in the diameter of the balloon 3, particularly at the inflatable portion 3B, at the time of inflation, the balloon catheter 1A can reduce stress applied to the blood vessel that is in a normal state. Furthermore, the balloon catheter 1A can improve durability of the inflatable portion 3B of the balloon 3.

Special Notes Relating to First Embodiment

The inflatable portion 3B of the balloon 3 is not limited to being the tube shape. The diameter of the inflatable portion 3B may change over the extending direction. The cross section of the inflatable portion 3B is not limited to being circular, and may be an elliptical shape or a polygonal shape. In this case, the outer radius Ro(1) of the inflatable portion 3B need not necessarily be the same at the inner side thick film portion 4A and the thin film portions 40.

The shape of the inner side thick film portion 4A is not limited to that of the above-described embodiment, and various changes are possible. The number of the inner side thick film portions 4A extending in the extending direction is not limited to three, and may be one, two, or four or more. The inner side thick film portion 4A needs not necessarily be provided extending from the distal end portion 30D to the proximal end portion 30P of the inflatable portion 3B. For example, the inner side thick film portion 4A may be cut at portions thereof in the extending direction.

Of the protruding portion 300 formed in the inner surface 301 of the inner side thick film portion 4A, a distal end portion in the vicinity of the center axis C1 may be pointed, or may be smooth. The thickness of the inner side thick film portion 4A may become smaller the closer to the distal end portion 30D. The thickness of the inner side thick film portion 4A may become smaller the closer to the proximal end portion 30P.

Second Embodiment (Balloon Catheter 1B)

Figure 2:
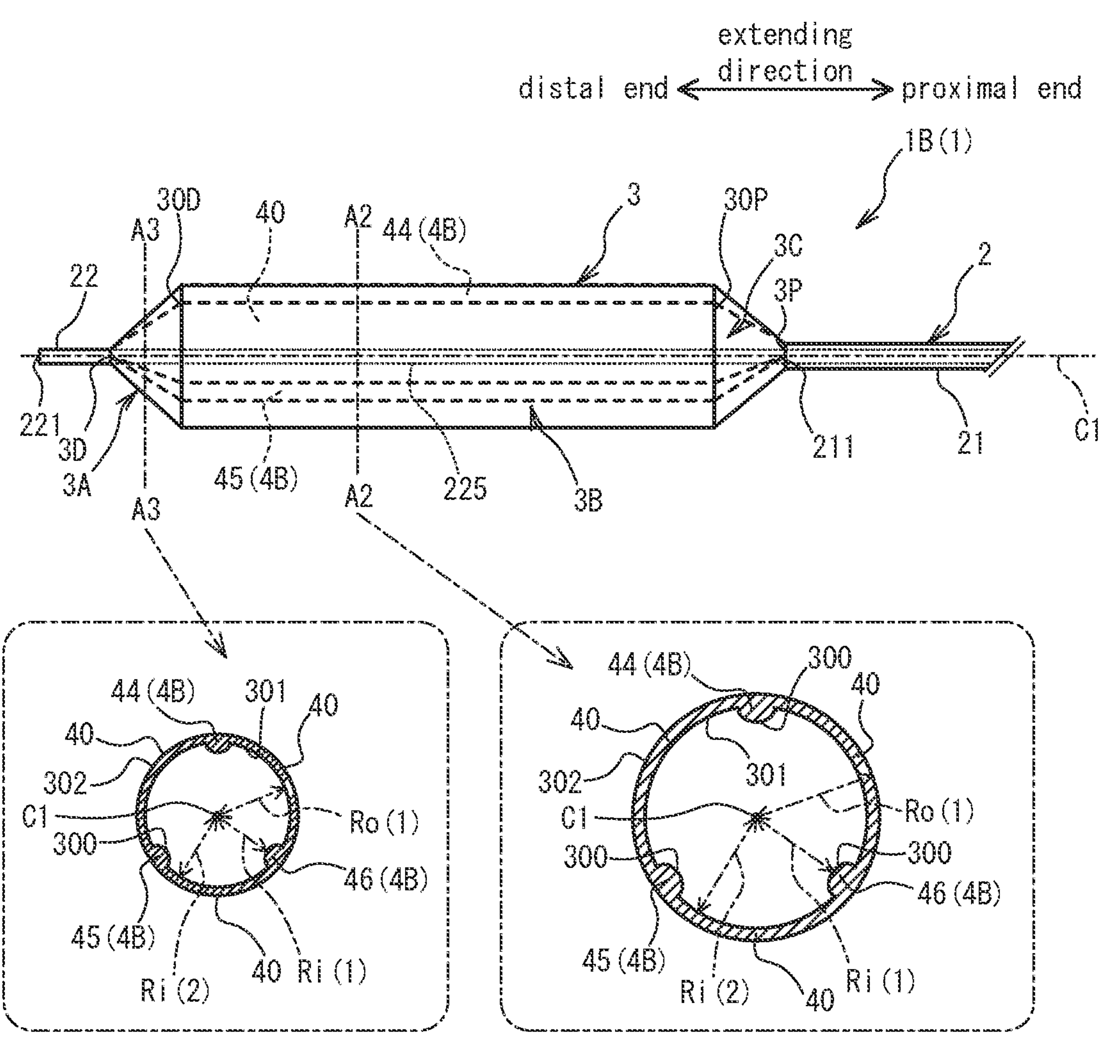
FIG. 2 is a view of a balloon catheter, and a cross-sectional view when the balloon catheter is cut on a plane orthogonal to the extending direction.

The balloon catheter 1B will be described with reference to FIG. 2. The balloon catheter 1B differs from the balloon catheter 1A in that an inner side thick film portion 4B is provided not only at the inflatable portion 3B of the balloon 3, but also at the distal end connecting portion 3A and the proximal end connecting portion 3C.

The distal end connecting portion 3A, the inflatable portion 3B, and the proximal end connecting portion 3C include inner side thick film portions 44, 45, and 46 (hereinafter referred to as the inner side thick film portion 4B when there is no particular distinction to be made), and the thin film portions 40. The inner side thick film portion 4B extends in the extending direction from the distal end portion 3D of the distal end connecting portion 3A to the proximal end portion 3P of the proximal end connecting portion 3C. The thickness of the inner side thick film portion 4B at the inflatable portion 3B is uniform from the distal end portion 30D to the proximal end portion 30P. Thus, the inner radius Ri(1) at the inner side thick film portion 4B is uniform from the distal end portion 30D to the proximal end portion 30P. In other words, the protrusion amount, toward the center axis C1, of the protruding portion 300 formed at the inner surface 301 of the inner side thick film portion 4B is uniform from the distal end portion 30D to the proximal end portion 30P.

On the other hand, the thickness of the inner side thick film portion 4B at the distal end connecting portion 3A becomes gradually thinner from a section, of the distal end connecting portion 3A, connected to the distal end portion 30D of the inflatable portion 3B toward the distal end portion 3D. In other words, the protrusion amount, toward the center axis C1, of the protruding portion 300 formed in the inner surface 301 of the inner side thick film portion 4B becomes gradually smaller from the distal end portion 30D toward the distal end portion 3D.

Further, the thickness of the inner side thick film portion 4B at the proximal end connecting portion 3C becomes gradually thinner from a section, of the proximal end connecting portion 3C, connected to the proximal end portion 30P of the inflatable portion 3B toward the proximal end portion 3P. In other words, the protrusion amount, toward the center axis C1, of the protruding portion 300 formed in the inner surface 301 of the inner side thick film portion 4B becomes gradually smaller from the proximal end portion 30P toward the proximal end portion 3P.

Operations and Effects of Second Embodiment

In the balloon catheter 1B, the inner side thick film portion 4B is provided from the distal end portion 3D of the distal end connecting portion 3A to the proximal end portion 3P of the proximal end connecting portion 3C, of the balloon 3. In this case, the balloon catheter 1B can suppress the rapid expansion and contraction in the extending direction at the time of deflation or inflation over the whole region of the distal end connecting portion 3A and the proximal end connecting portion 3C, not just the whole region of the inflatable portion 3B.

The thickness of the inner side thick film portion 4B at the distal end connecting portion 3A becomes gradually thinner from the section connected to the distal end portion 30D of the inflatable portion 3B toward the distal end portion 3D. The thickness of the inner side thick film portion 4B at the proximal end connecting portion 3C becomes gradually thinner from the section connected to the proximal end portion 30P of the inflatable portion 3B toward the proximal end portion 3P. In this case, the balloon catheter 1B can cause the distal end portion 3D of the distal end connecting portion 3A and the proximal end portion 3P of the proximal end connecting portion 3C of the balloon 3 to be softer. Thus, when these portions are in contact with the stent, a hard lesion, or the like, a state in which the balloon 3 is held in a fully extended state in the extending direction can be suppressed. As a result, it is possible to suppress an unnecessary force from the balloon 3 from acting against the stent, the hard lesion, or the like.

Special Notes Relating to Second Embodiment

The balloon 3 may include the inner side thick film portion 4B at the distal end connecting portion 3A only, and need not necessarily include the inner side thick film portion 4B at the proximal end connecting portion 3C. The balloon 3 may include the inner side thick film portion 4B at the proximal end connecting portion 3C only, and need not necessarily include the inner side thick film portion 4B at the distal end connecting portion 3A. The thickness of the inner side thick film portion 4B at the distal end connecting portion 3A may be uniform from the section connected to the distal end portion 30D of the inflatable portion 3B toward the distal end portion 3D. The thickness of the inner side thick film portion 4B at the proximal end connecting portion 3C may be uniform from the section connected to the proximal end portion 30P of the inflatable portion 3B toward the proximal end portion 3P.

Third Embodiment (Balloon Catheter 1C)

Figure 3:
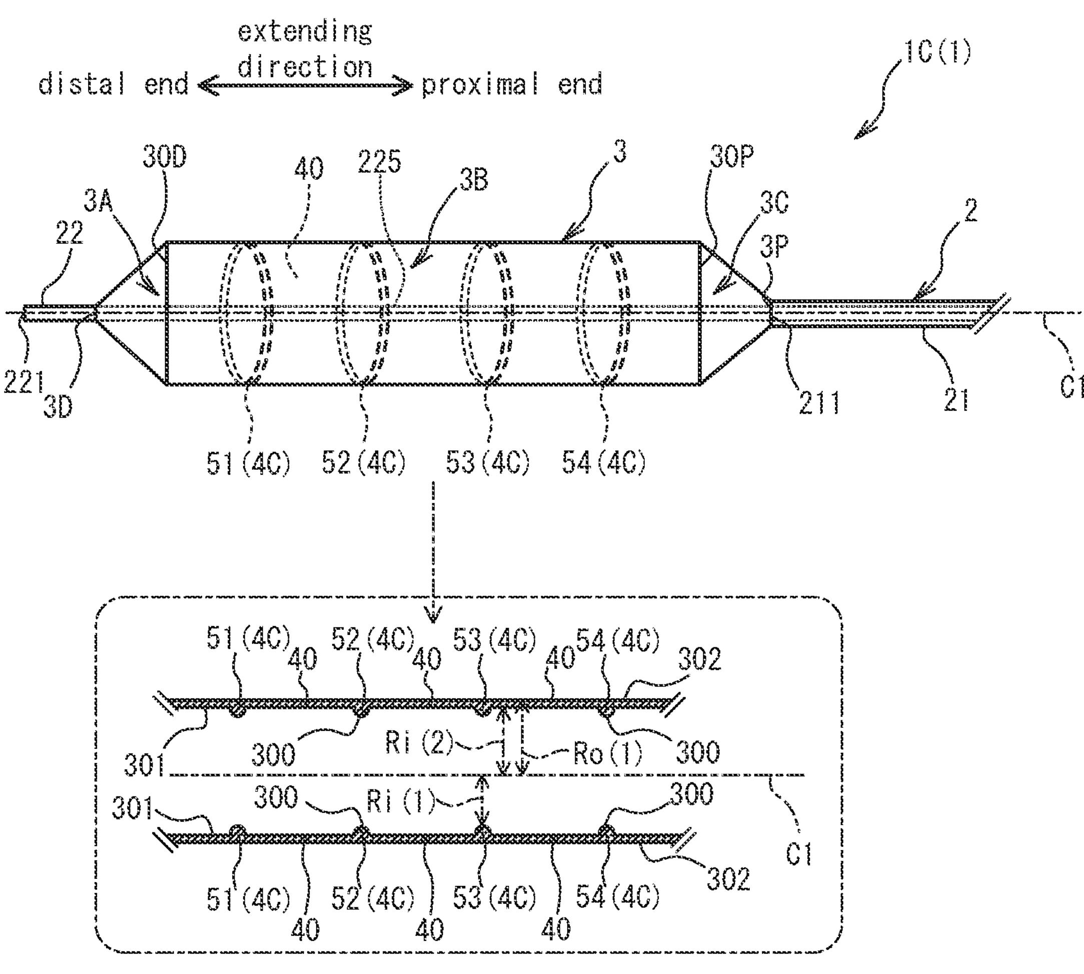
FIG. 3 is a view of a balloon catheter, and a cross-sectional view when the balloon catheter is cut on a plane orthogonal to the extending direction.

The balloon catheter 1C will be described with reference to FIG. 3. The balloon catheter 1C differs from the balloon catheter 1A in that the inflatable portion 3B includes inner side thick film portion 4C having a different shape from that of the inner side thick film portion 4A (refer to FIG. 1).

The inflatable portion 3B includes inner side thick film portions 51, 52, 53 and 54 (hereinafter referred to as the inner side thick film portion 4C when there is no particular distinction to be made), and the thin film portions 40. The inner side thick film portion 4C extends in an annular shape along the circumferential direction centered on the center axis C1. The inner side thick film portions 51, 52, 53 and 54 are arranged at equal intervals in the extending direction. The thickness of the inner side thick film portions 51, 52, 53 and 54 is uniform over the circumferential direction. Thus, the inner radius Ri(1) of the inner side thick film portion 4C is uniform over the circumferential direction. In other words, the protrusion amount, toward the center axis C1, of the protruding portion 300 formed in the inner surface 301 of the inner side thick film portion 4C is uniform over the circumferential direction.

Operations and Effects of Third Embodiment

Since the inner side thick film portion 4C of the balloon catheter 1C extends in the annular shape, even when the thickness of the thin film portions 40 is thin, it is possible to maintain the high pressure resistance of the balloon 3 over the whole region of the inflatable portion 3B in the circumferential direction. Further, the balloon catheter 1C can improve flexibility when the balloon 3 curves in a direction intersecting the extending direction.

Special Notes Relating to Third Embodiment

The number of the inner side thick film portions 4C is not limited to that of the above-described embodiment, and may be one to three, or five or more. Part of the inner side thick film portion 4C in the circumferential direction may be cut. The thicknesses of the inner side thick film portions 51 to 54 may be different from each other. For example, the thicknesses of the inner side thick film portions 51 to 54 may be thinner the closer to the distal end portion 30D of the inflatable portion 3B. The thickness of each of the inner side thick film portions 51 to 54 needs not necessarily be uniform in the circumferential direction. Inner side thick film portions (the inner side thick film portion 4A according to the first embodiment, for example) that connect the inner side thick film portions 51 to 54 may extend in the extending direction. The annular inner side thick film portion 4C may also be provided at the distal end connecting portion 3A and the proximal end connecting portion 3C.

Fourth Embodiment (Balloon Catheter 1D)

Figure 4:
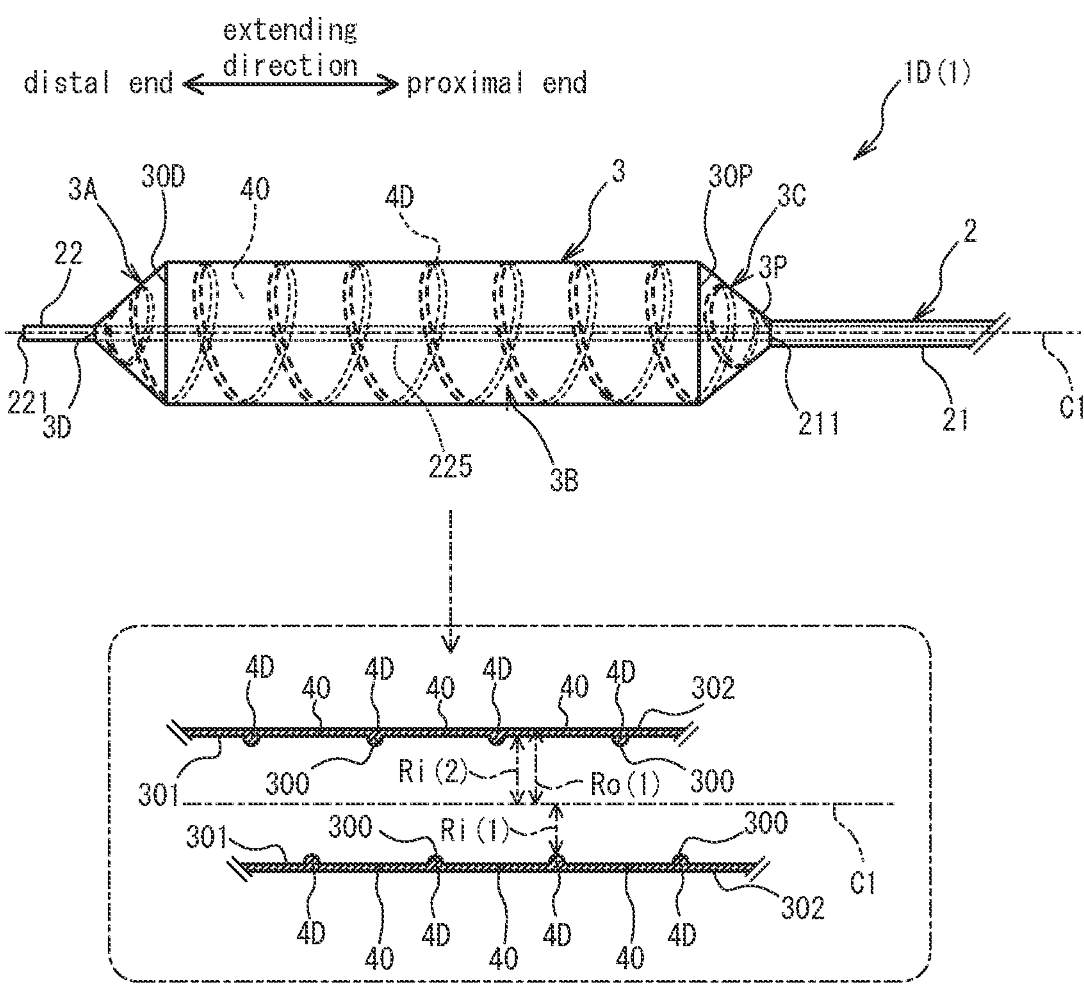
FIG. 4 is a view of a balloon catheter, and a cross-sectional view when the balloon catheter is cut on a plane orthogonal to the extending direction.

The balloon catheter 1D will be described with reference to FIG. 4. The balloon catheter 1D differs from the balloon catheter 1B in that the proximal end connecting portion 3C, the inflatable portion 3B, and the distal end connecting portion 3A include an inner side thick film portion 4D having a different shape from that of the inner side thick film portion 4B (refer to FIG. 2).

The distal end connecting portion 3A, the inflatable portion 3B, and the proximal end connecting portion 3C include the inner side thick film portion 4D and the thin film portions 40. The inner side thick film portion 4D extends in a spiral shape along the circumferential direction centered on the center axis C1. The inner side thick film portion 4D is provided between the distal end portion 30D and the proximal end portion 30P of the inflatable portion 3B, between the section of the distal end connecting portion 3A connected to the distal end portion 30D of the inflatable portion 3B and the distal end portion 3D, and between the section of the proximal end connecting portion 3C connected to the proximal end portion 30P of the inflatable portion 3B and the proximal end portion 3P. In other words, the inner side thick film portion 4D extends in the spiral shape between the distal end portion 3D of the distal end connecting portion 3A and the proximal end portion 3P of the proximal end connecting portion 3C.

The thickness of the inner side thick film portion 4D is uniform over the whole region from the distal end portion 3D to the proximal end portion 3P. Thus, inner radius Ri(1) of the inner side thick film portion 4D is uniform over the whole region from the distal end portion 3D to the proximal end portion 3P. Further, a helical pitch of the inner side thick film portion 4D is uniform over the whole region from the distal end portion 3D to the proximal end portion 3P.

Operations and Effects of Fourth Embodiment

The balloon catheter 1D includes the spiral shaped inner side thick film portion 4D at the inflatable portion 3B. Thus, the balloon catheter 1D can arrange the inner side thick film portion 4D seamlessly in the extending direction of the inflatable portion 3B. As a result, the balloon catheter 1D can maintain the high pressure resistance of the balloon 3 over the extending direction of the inflatable portion 3B. Further, the balloon catheter 1D can improve the flexibility when the inflatable portion 3B of the balloon 3 curves in a direction intersecting the extending direction.

The balloon catheter 1D further includes the inner side thick film portion 4D at the distal end connecting portion 3A and the proximal end connecting portion 3C. Thus, the inner side thick film portion 4D extends between the distal end portion 3D of the distal end connecting portion 3A and the proximal end portion 3P of the proximal end connecting portion 3C. In this case, the balloon catheter 1D can arrange the inner side thick film portion 4D seamlessly over the whole region, in the extending direction, between the distal end portion 3D and the proximal end portion 3P of the balloon 3. Thus, the balloon catheter 1D can maintain the high-pressure resistance of the balloon 3 over a wider range in the extending direction.

Special Notes Relating to Fourth Embodiment

The inner side thick film portion 4D may be provided only at the inflatable portion 3B, and need not necessarily be provided at the distal end connecting portion 3A and the proximal end connecting portion 3C. The thickness of the inner side thick film portion 4D need not necessarily be uniform. For example, the thickness of the inner side thick film portion 4D may become smaller the closer to the distal end portion 30D or the proximal end portion 30P. The helical pitch of the inner side thick film portion 4D need not necessarily be uniform. For example, the helical pitch of the inner side thick film portion 4D may become smaller the closer to the distal end portion 30D or the proximal end portion 30P.

Fifth Embodiment (Balloon Catheter 1E)

Figure 5:
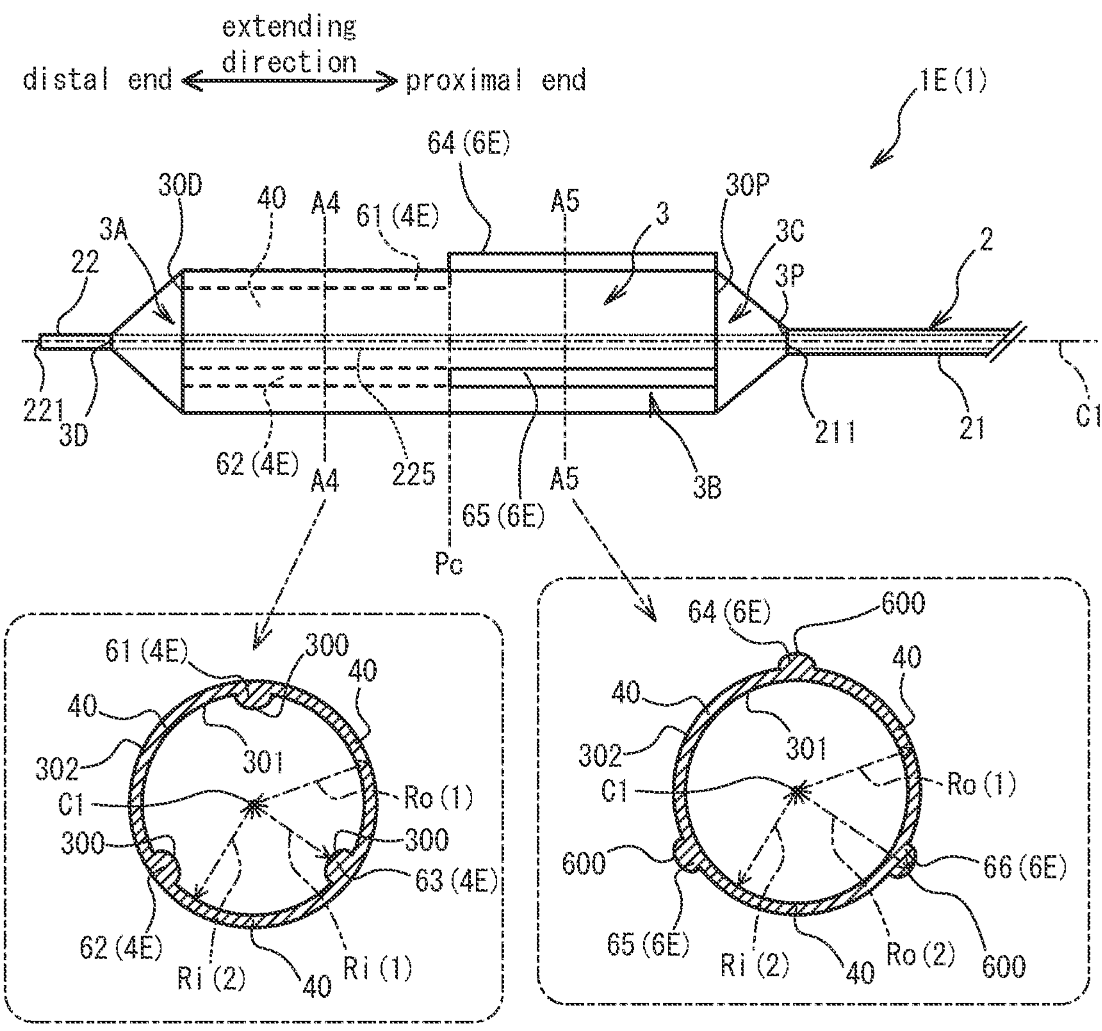
FIG. 5 is a view of a balloon catheter, and a cross-sectional view when the balloon catheter is cut on a plane orthogonal to the extending direction.

The balloon catheter 1E will be described with reference to FIG. 5. The balloon catheter 1E differs from the balloon catheter 1A in that the inflatable portion 3B includes an inner side thick film portion 4E and an outer side thick film portion 6E in place of the inner side thick film portion 4A (refer to FIG. 1). Hereinafter, a position at the center of the inflatable portion 3B in the extending direction will be referred to as a center position Pc.

The inflatable portion 3B includes inner side thick film portions 61, 62, and 63 (hereinafter referred to as the inner side thick film portion 4E when there is no particular distinction to be made), outer side thick film portions 64, 65, and 66 (hereinafter referred to as the outer side thick film portion 6E when there is no particular distinction to be made), and the thin film portions 40.

The inner side thick film portions 61, 62, and 63 are arranged at equal intervals in the circumferential direction centered on the center axis C1. The inner side thick film portion 4E extends along the extending direction between the distal end portion 30D of the inflatable portion 3B and the center position Pc. In other words, the inner side thick film portion 4E is arranged at the position approaching the distal end portion 30D from the center position Pc. Of the inflatable portion 3B, the outer radius R0(1) of the section approaching the distal end portion 30D from the center position Pc is the same at both the inner side thick film portion 4E and the thin film portions 40. Thus, the outer surface 302 at this section is smooth and has no indentations and protrusions. On the other hand, of the inflatable portion 3B, the inner radius Ri(n) of the section approaching the distal end portion 30D from the center position Pc differs at the inner side thick film portion 4E and at the thin film portions 40. The inner radius Ri(1) at the inner side thick film portion 4E is smaller than the inner radius Ri(2) at the thin film portions 40. Thus, the inner surface 301 at this section protrudes toward the inner side at the inner side thick film portion 4E and the protruding portion 300 is formed.

The thickness of the inner side thick film portion 4E is uniform from the distal end portion 30D to the center position Pc. Thus, the inner radius Ri(1) at the inner side thick film portion 4E is uniform from the distal end portion 30D to the center position Pc. In other words, the protrusion amount, toward the center axis C1, of the protruding portion 300 formed in the inner surface 301 of the inner side thick film portion 4E is uniform from the distal end portion 30D to the center position Pc.

The thickness of the outer side thick film portion 6E is different from that of the thin film portions 40, and matches that of the inner side thick film portion 4E. The thickness of the outer side thick film portion 6E is greater than the thickness of the thin film portions 40. The outer side thick film portions 64, 65, and 66 are arranged at equal intervals in the circumferential direction centered on the center axis C1.

The outer side thick film portion 6E is arranged at the position approaching the proximal end portion 30P from the center position Pc. Of the inflatable portion 3B, the inner radius Ri(2) of the section approaching the proximal end portion 30P from the center position Pc is the same at both the outer side thick film portion 6E and the thin film portions 40. Thus, the inner surface 301 of this section is smooth and has no indentations and protrusions. On the other hand, of the inflatable portion 3B, the outer radius Ro(n) of the section approaching the proximal end portion 30P from the center position Pc differs at the outer side thick film portion 6E and at the thin film portions 40. The outer radius Ro(2) at the outer side thick film portion 6E is larger than the outer radius Ro(1) at the thin film portions 40. Thus, the outer surface 302 of this section protrudes toward the outer side at the outer side thick film portion 6E. Hereinafter, these sections will be referred to as a protruding portion 600. The outer side thick film portion 6E extends in the extending direction between the center position Pc of the inflatable portion 3B and the proximal end portion 30P.

The thickness of the outer side thick film portion 6E is uniform from the center position Pc to the proximal end portion 30P. Thus, the outer radius Ro(2) of the outer side thick film portion 6E is uniform from the center position Pc to the proximal end portion 30P. In other words, a protrusion amount, toward the outer side, of the protruding portion 600 formed in the outer surface 302 of the outer side thick film portion 6E is uniform from the center position Pc to the proximal end portion 30P.

Operations and Effects of Fifth Embodiment

The balloon 3 of the balloon catheter 1E is provided with the inner side thick film portion 4E at the position approaching the distal end portion 30D from the center position Pc, and with the outer side thick film portion 6E at the position approaching the proximal end portion 30P from the center position Pc. Of the inflatable portion 3B of the balloon 3, the outer side thick film portion 6E is not provided at the position approaching the distal end portion 30D. Thus, compared to a case in which the outer side thick film portion 6E is provided over the whole region in the extending direction of the inflatable portion 3B, it is difficult for the balloon 3 to be held in the fully extended state in the extending direction. Thus, for example, at a stage at which the balloon 3 is inserted into the blood vessel in which the stent has been placed, even if the outer side thick film portion 6E becomes caught up on the stent, it is possible to suppress the balloon 3 from being held in the fully extended state in the extending direction. Thus, the balloon catheter 1E can suppress unnecessary force from acting on the stent from the balloon 3. Further, the balloon catheter 1E can cause the outer side thick film portion 6E to operate on the lesion inside the blood vessel at the time of inflating the balloon 3.

Special Notes Relating to Fifth Embodiment

A boundary section between the inner side thick film portion 4E and the outer side thick film portion 6E is not limited to being the center position Pc. For example, of two dividing lines dividing the inflatable portion 3B into three equal sections in the extending direction, the boundary section between the inner side thick film portion 4E and the outer side thick film portion 6E may be positioned at the position of the dividing line closer to the distal end portion 30D. Further, for example, of the two dividing lines dividing the inflatable portion 3B into three equal sections in the extending direction, the boundary section between the inner side thick film portion 4E and the outer side thick film portion 6E may be positioned at the position of the dividing line closer to the proximal end portion 30P.

The inner side thick film portion 4E may be provided at the distal end connecting portion 3A also. In this case, the inner side thick film portion 4E may extend in the extending direction between the section, of the distal end connecting portion 3A, connected to the distal end portion 30D of the inflatable portion 3B and the distal end portion 3D. The outer side thick film portion 6E may be provided at the proximal end connecting portion 3C also. In this case, the outer side thick film portion 6E may extend in the extending direction between the section, of the proximal end connecting portion 3C, connected to the proximal end portion 30P of the inflatable portion 3B and the proximal end portion 3P.

The thickness of the inner side thick film portion 4E, and the thickness of the outer side thick film portion 6E need not necessarily be uniform in the extending direction. For example, the thickness of the inner side thick film portion 4E and the outer side thick film portion 6E may become gradually smaller toward the center position Pc. The thickness of the inner side thick film portion 4E may become gradually smaller toward the distal end portion 30D. The thickness of the outer side thick film portion 6E may become gradually smaller toward the proximal end portion 30P.

The inner surface 301 of the inflatable portion 3B may protrude to the inner side at the outer side thick film portion 6E. In other words, at the outer side thick film portion 6E, the outer surface 302 may protrude to the outer side, and the inner surface 301 may protrude to the inner side.

Sixth Embodiment (Balloon Catheter 1F)

Figure 6:
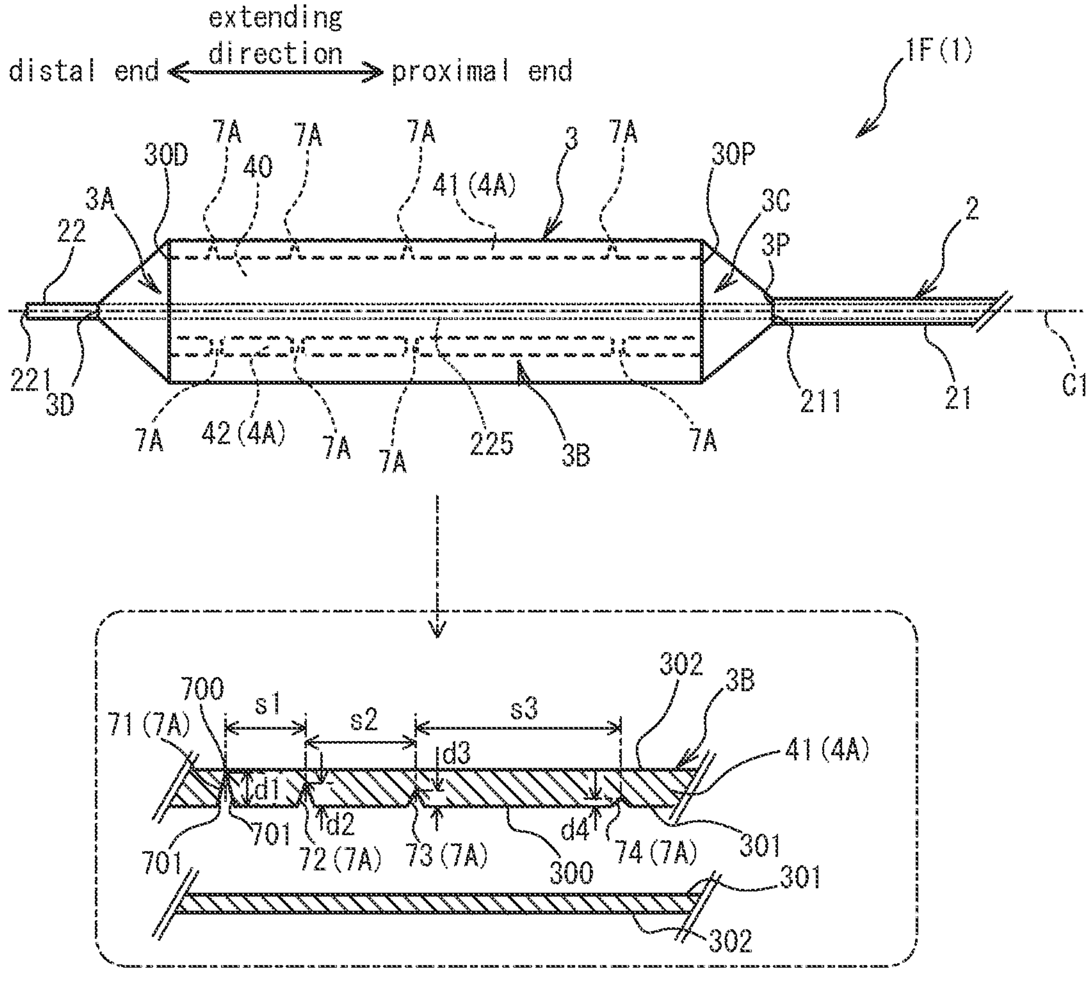
FIG. 6 is a view of a balloon catheter, and a cross-sectional view when the balloon catheter is cut on a plane orthogonal to the extending direction.

The balloon catheter 1F will be described with reference to FIG. 6. The balloon catheter 1F differs from the balloon catheter 1A in that a slit 7A is provided in the inner side thick film portion 4A.

In the balloon catheter 1F, slits 71, 72, 73, and 74 (hereinafter referred to as the slit 7A when there is no particular distinction to be made) are provided in each of the inner side thick film portions 41 to 43. The slit 7A is cuts or notches provided in the protruding portion 300 of the inner side thick film portion 4A. The slit 7A includes a pair of wall portions 701 facing each other in the extending direction. The pair of wall portions 701 are connected at the deepest section of the slit 7A (hereinafter referred to as a bottom portion 700). When the slit 7A is the cut, the pair of wall portions 701 are in contact with each other. When the slit 7A is the notch, the pair of wall portions 701 are separated in the extending direction. Further, when the slit 7A is the notch, an interval in the extending direction between the pair of wall portions 701 becomes smaller the deeper the depth of the slit 7A. In FIG. 6, the slit 7A that is the notch is exemplified.

The slits 71, 72, 73, and 74 are arranged in that order in the extending direction. The slit 71 is closest to the distal end portion 30D of the inflatable portion 3B of the balloon 3. The slit 74 is closest to the proximal end portion 30P of the inflatable portion 3B of the balloon 3. An interval in the extending direction between the slits 71 and 72 is denoted by s1. An interval in the extending direction between the slits 72 and 73 is denoted by s2. An interval in the extending direction between the slits 73 and 74 is denoted by s3. The interval s2 is larger than the interval s1, and the interval s3 is larger than the interval s2. In other words, the closer to the distal end portion 30D of the inflatable portion 3B of the balloon 3, the narrower the interval s between the slits 71 to 74.

The depth of the slit 71 is denoted by d1. The depth of the slit 72 is denoted by d2. The depth of the slit 73 is denoted by d3. The depth of the slit 74 is denoted by d4. The depth d of the slit 7A corresponds to a length, in the radial direction, from the inner surface 301 of the balloon 3 to the bottom portion 700. The depth d2 is smaller than the depth d1. The depth d3 is smaller than the depth d2. The depth d4 is smaller than the depth d3. In other words, the closer to the distal end portion 30D of the inflatable portion 3B of the balloon 3, the deeper the depth d of each of the slits 71 to 74.

Operations and Effects of Sixth Embodiment

In the balloon catheter 1F, since the inner side thick film portion 4A is caused to curve by the slit 7A, the balloon 3 can be caused to change shape in an excellent manner even in a meandering blood vessel. Thus, the balloon catheter 1F can have excellent trackability of the balloon 3 in the blood vessel.

The interval s between each of the slits 71 to 74 in the extending direction becomes narrower the closer to the distal end portion 30D of the inflatable portion 3B. Here, the balloon 3 bends more easily the closer to the distal end portion 30D at which the interval s between the slits 71 to 74 is narrower. In this case, when the balloon 3 is inserted into the meandering blood vessel or the like, the balloon 3 easily tracks the blood vessel. Thus, the user can cause the balloon 3 to appropriately reach a target location. On the other hand, the rigidity of the balloon 3 increases the closer to the proximal end portion 30P at which the interval s between the slits 71 to 74 is wider. In this case, since the balloon 3 can increase the pressure applied to the lesion of the blood vessel, it is possible to improve treatment efficiency by the inflation of the balloon 3.

The depth d of each of the slits 71 to 74 becomes deeper the closer to the distal end portion 30D. Here, the balloon 3 bends more easily the closer to the distal end portion 30D at which the depth d of the slits 71 to 74 is deeper. In this case, when the balloon 3 is inserted into the meandering blood vessel or the like, the balloon 3 easily tracks the blood vessel. Thus, the user can cause the balloon 3 to appropriately reach the target location. On the other hand, the rigidity of the balloon 3 increases the closer to the proximal end portion 30P at which the depth d of the slits 71 to 74 is shallower. In this case, since the balloon 3 can increase the pressure applied to the lesion of the blood vessel, it is possible to improve the treatment efficiency by the inflation of the balloon 3.

Special Notes Relating to Sixth Embodiment

The number of the slits 7A is not limited to that of the above-described embodiment, and may be one to three, or may be five or more. A different number of the slits 7A may be provided in each of the inner side thick film portions 41 to 43. The positions of the slits 71 to 74 in the extending direction may be different for each of the inner side thick film portions 41 to 43. The slits 71 to 74 having the respectively different depths d may be arranged at equal intervals in the extending direction. The depth d of the slits 71 to 74 arranged at the respectively different intervals s may be the same for all of the slits 71 to 74. The slits 71 to 74 having the same depth d may be arranged at the equal intervals in the extending direction.

Seventh Embodiment (Balloon Catheter 1G)

Figure 7:
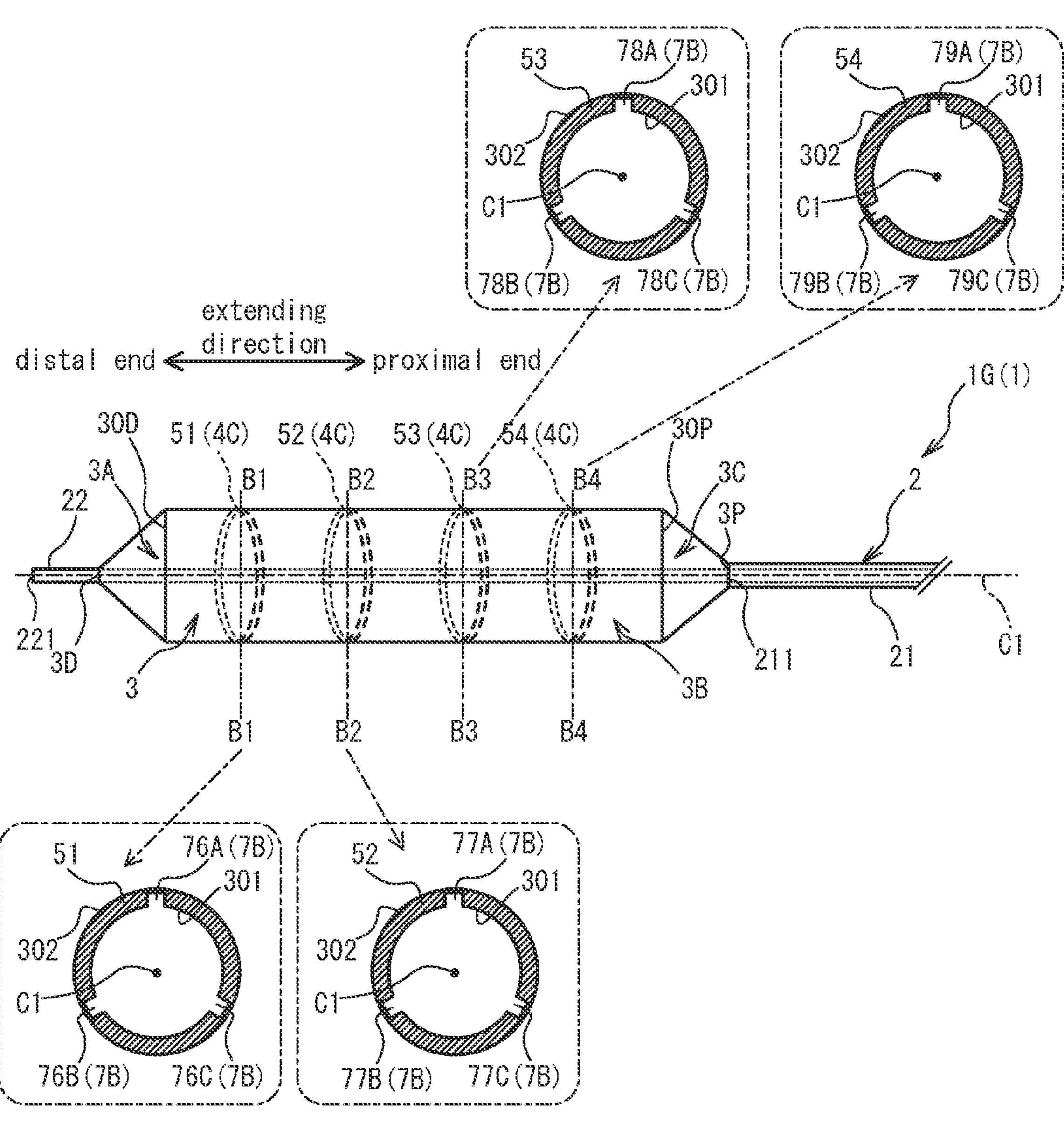
FIG. 7 is a view of a balloon catheter, and a cross-sectional view when the balloon catheter is cut on a plane orthogonal to the extending direction.

The balloon catheter 1G will be described with reference to FIG. 7. The balloon catheter 1G differs from the balloon catheter 1C (refer to FIG. 3) in that a slit 7B are provided in the annular inner side thick film portion 4C.

Slits 76A, 76B, and 76C are provided in an inner side thick film portion 51 of the inflatable portion 3B. Slits 77A, 77B, and 77C are provided in an inner side thick film portion 52. Slits 78A, 78B, and 78C are provided in an inner side thick film portion 53. Slits 79A, 79B, and 79C are provided in an inner side thick film portion 54. When no particular distinction is made between each of the slits 76A to 76C, 77A to 77C, 78A to 78C, and 79A to 79C, they will be referred to as the slit 7B.

The slits 76A to 76C, 77A to 77C, 78A to 78C, and 79A to 79C are respectively arranged at equal intervals in the circumferential direction centered on the center axis C1. The positions of the slits 76A, 77A, 78A, and 79A are aligned with each other in the circumferential direction. The positions of the slits 76B, 77B, 78B, and 79B are aligned with each other in the circumferential direction. The positions of the slits 76C, 77C, 78C, and 79C are aligned with each other in the circumferential direction. Thus, when viewed from the extending direction, of the slit 7B, the positions of the slits 76A, 77A, 78A, and 79A overlap each other, the positions of the slits 76B, 77B, 78B, and 79B overlap each other, and the positions of the slits 76C, 77C, 78C, and 79C overlap each other.

Operations and Effects of Seventh Embodiment

Since the balloon catheter 1G can cause the annular inner side thick film portion 4C to bend using the slit 7B, it is possible to change shape in an excellent manner even in the meandering blood vessel. It is thus possible to cause the balloon 3 to have excellent trackability with respect to the blood vessel.

When the balloon 3 is viewed from the extending direction, the positions of the slits 76A, 77A, 78A, and 79A overlap each other, the positions of the slits 76B, 77B, 78B, and 79B overlap each other, and the positions of the slits 76C, 77C, 78C, and 79C overlap each other. In this way, the balloon catheter 1G can cause the portion at which the slit 7B is provided in the circumferential direction of the balloon 3 to be portion having high bendability, and can cause portion at which the slit 7B is not provided to be portions having low bendability. In this case, by bending the balloon 3 at the portions having the high bendability, the balloon 3 more easily tracks the blood vessel when the balloon 3 is inserted into the meandering blood vessel or the like. Thus, the user can cause the balloon 3 to appropriately reach the target location.

Special Notes Relating to Seventh Embodiment

The number and positions of the slits 7B provided in each of the inner side thick film portions 51 to 54 may be mutually different. The slit 7B needs not necessarily be provided in some of the inner side thick film portions 51 to 54 (the inner side thick film portion 54 closest to the proximal end portion 3P, for example). All of the slits 7B need not necessarily overlap each other. For example, only the positions of the slits 76A, 77A, 78A, and 79A may overlap each other, and the positions of the slits 76B, 77B, 78B, and 79B and the positions of the slits 76C, 77C, 78C, and 79C need not necessarily overlap each other.

While the invention has been described in conjunction with various example structures outlined above and illustrated in the figures, various alternatives, modifications, variations, improvements, and/or substantial equivalents, whether known or that may be presently unforeseen, may become apparent to those having at least ordinary skill in the art. Accordingly, the example embodiments of the disclosure, as set forth above, are intended to be illustrative of the invention, and not limiting the invention. Various changes may be made without departing from the spirit and scope of the disclosure. Therefore, the disclosure is intended to embrace all known or later developed alternatives, modifications, variations, improvements, and/or substantial equivalents.

What is claimed is:

1. A balloon for a catheter comprising:

an inflatable portion having a tube shape and extending in an extending direction;

a distal end connecting portion being a portion extending from a first distal end portion of the inflatable portion that is on one side in the extending direction of the inflatable portion, to a second distal end portion of the balloon, a diameter of a third proximal end portion of the distal end connecting portion connected to the inflatable portion being larger than a diameter of the second distal end portion of the balloon that is on the opposite side from the third proximal end portion connected to the inflatable portion; and a proximal end connecting portion being a portion extending from a first proximal end portion of the inflatable portion that is on another side in the extending direction of the inflatable portion to a second proximal end portion of the balloon, a diameter of a third distal end portion of the proximal end connecting portion connected to the inflatable portion being larger than a diameter of the second proximal end portion of the balloon that is on the opposite side from the third distal end portion connected to the inflatable portion, wherein wherein the balloon for the catheter includes an inner side thick film portion and a thin film portion having differing thicknesses from each other, the thickness of the inner side thick film portion is greater than the thickness of the thin film portion, an inner surface at the inner side thick film portion protrudes further inward than an inner surface at the thin film portion, in a radial direction centered on a center axis extending in the extending direction and passing through a center of the inflatable portion, an outer surface at the inner side thick film portion does not protrude further outward in the radial direction than an outer surface at the thin film portion, the inner side thick film portion is provided at the inflatable portion, the distal end connecting portion, and the proximal end connecting portion, the inner side thick film portion extends along the extending direction from the second distal end portion to the second proximal end portion, the thickness of the inner side thick film portion of the distal end connecting portion becomes gradually thinner from a portion connected to the first distal end portion of the inflatable portion toward the second distal end portion, and the thickness of the inner side thick film portion of the proximal end connecting portion becomes gradually thinner from a portion connected to the first proximal end portion of the inflatable portion toward the second proximal end portion.

2. The balloon for the catheter according to claim 1, wherein, at any position along the extending direction in each cross-sectional portion of the inflatable portion, the distal end connecting portion and the proximal end connecting portion are obtained by cutting along a plane perpendicular to the extending direction, an outer diameter, which is a distance in the radial direction from the center axis to the outer surface, is the same at the thin film portion and at the inner side thick film portion, and an inner diameter, which is a distance in the radial direction from the center axis to the inner surface, is smaller at the inner side thick film portion than at the thin film portion.

3. The balloon for the catheter according to claim 1, wherein at least one slit is provided in the inner side thick film portion.

4. The balloon for the catheter according to claim 3, wherein the at least one slit comprises a plurality of slits, the plurality of slits are provided being arrayed in the extending direction, and an interval between each of the plurality of slits in the extending direction becomes smaller the closer to the second distal end portion.

5. The balloon for the catheter according to claim 3, wherein the at least one slit comprises a plurality of slits, the plurality of slits are provided being arrayed in the extending direction, and a depth of each of the plurality of slits becomes deeper the closer to the second distal end portion.

6. The balloon for the catheter according to claim 1, wherein the inner side thick film portion is a helical shape extending along a circumferential direction centered on the center axis, and is provided between the first distal end portion and the first proximal end portion.

7. The balloon for the catheter according to claim 1, wherein a plurality of slits are provided in the inner side thick film portion, the plurality of slits are provided being arrayed in a direction in which the inner side thick film portion extends, and when viewed from the extending direction, each of the plurality of slits is disposed at a position overlapping with at least one other of the plurality of slits.

* * * * *